United States Patent
Talos et al.

[19]

[11] Patent Number: 6,053,919
[45] Date of Patent: Apr. 25, 2000

[54] BONE FRAGMENT-FIXING DEVICE

[75] Inventors: Gilbert Talos, Oberdorf, Switzerland; Ulrich Joos, Münster, Germany

[73] Assignee: Synthes (U. S. A), Paoli, Pa.

[21] Appl. No.: 08/981,102

[22] PCT Filed: Jul. 3, 1995

[86] PCT No.: PCT/EP95/02567

§ 371 Date: Jun. 11, 1998

§ 102(e) Date: Jun. 11, 1998

[87] PCT Pub. No.: WO97/01991

PCT Pub. Date: Jan. 23, 1997

[51] Int. Cl.[7] .................................................. A61B 17/58
[52] U.S. Cl. ................................................ 606/71; 606/72
[58] Field of Search ............................... 606/61, 64, 69, 606/70, 71, 72, 75

[56] References Cited

U.S. PATENT DOCUMENTS

| | | |
|---|---|---|
| 2,406,832 | 9/1946 | Hardinge ................................... 128/87 |
| 4,696,290 | 9/1987 | Steffee ...................................... 606/61 |
| 5,290,288 | 3/1994 | Vignaud et al. .......................... 606/61 |
| 5,344,421 | 9/1994 | Crook ........................................ 606/61 |
| 5,352,224 | 10/1994 | Westermann .............................. 606/61 |
| 5,470,333 | 11/1995 | Ray .......................................... 606/61 |

FOREIGN PATENT DOCUMENTS

| | | |
|---|---|---|
| 0 506 420 | 9/1992 | European Pat. Off. . |
| 0 507 162 | 10/1992 | European Pat. Off. . |
| 2 556 583 | 6/1985 | France . |

*Primary Examiner*—Michael Buiz
*Assistant Examiner*—Daphna Shai
*Attorney, Agent, or Firm*—Pennie & Edmonds LLP

[57] ABSTRACT

A bone fragment-fixing device including a longitudinal bone plate which is provided at each of its ends with two through-holes for screws and which is also provided with a central longitudinal hole extending in the direction of the longitudinal axis of the plate. In addition, a slide is provided and arranged on stems which laterally limit the central longitudinal hole, in such a way that the slide is movable in the direction of the longitudinal axis of the plate. The slide is provided with a longitudinal hole extending cross-wise to the longitudinal axis of the plate when the slide is mounted, thus permitting a three-dimensional adaptability of the device.

5 Claims, 3 Drawing Sheets ically suitable for orthognatic correc-
BONE FRAGMENT-FIXING DEVICE

FIELD OF THE INVENTION

The invention concerns a device for the fixation of bone fragments.

The device is particularly suitable for orthognatic corrections at the lower jaw.

BACKGROUND

In order to treat any malformations in the area of the jaw and face, osteotomies with subsequent relocation of the bone fragments are performed. To some extent, the process of fixation of the bone fragments thus obtained is difficult, since there are no congruent planes of bone after an osteotomy with relocation of the fragments has been performed. This situation is further aggravated in the case of lower-jaw osteotomies, since the position of the joint of the jaw, which is located in the proximal fragment should not be altered. These circumstances aggravate the performance of an accurately dimension-fitting osteosynthesis which must also be stable with regard to its function, which has been the objective aspired to for the past several years.

The disadvantage of all the already-known devices in this field, e.g. those according to the DE-C 23.40.880, lies in the fact that they are not sufficiently adaptable during the performance of an operation and that after the operation has been performed, they show practically no bending ability arising from the plate surface.

SUMMARY OF THE INVENTION

The invention aims to remedy these matters. It is the purpose of the invention to create a device for the fixation of bone fragments which, on the one hand, allows for adaptability during the performance of an operation when the bone fragments are adjusted in relation to each other, and which on the other hand allows for a certain flexibility of the device cross-wise to the plate surface.

The present invention comprises a bone fragment-fixing device including a longitudinal bone plate which is provided at each of its ends with at least one through-hole for receiving a screw and which is also provided with a central longitudinal extending in the direction of the longitudinal axis of the bone plate and having a length that is 45–60% of the total length of the bone plate. The device also includes a slide mounted on stems which laterally limit the central longitudinal hole. The slide is mounted on the stems in such a way that the slide is movable in the direction of the longitudinal axis of the plate. The slide has a longitudinal hole which extends cross-wise to the longitudinal axis of the plate.

In one embodiment, the width of the central longitudinal hole is 50–65% of the total width of the bone plate. According to another embodiment, the thickness of the bone plate amounts to 8–12% of the total width of the bone plate. In a final embodiment, the length of the longitudinal hole of the slide essentially corresponds to the width of the central longitudinal hole.

The invention also comprises a bone plate having first and second ends each provided with at least one through-hole for receiving a screw and a central longitudinal hole extending in the longitudinal axis of the bone plate and having a amounting to 45–60% of the total length of the bone plate. According to one embodiment, the width of the central longitudinal hole amounts to 50–65% of the total width of the bone plate. In another embodiment, the thickness of the bone plate amounts to 8–12% of the total width of the bone plate.

The main benefit among the advantages obtained via the invention lies in the fact that due to the device according to the invention, a great degree of flexibility is obtained during the process of adjustment of the bone fragments in relation to each other, particularly in the case of occlusion occurring during a maxillo-facial application. By means of the slide, placed onto the longitudinal bone plate and provided with a longitudinal hole extending cross-wise to the longitudinal axis of the plate, a limited 2-dimensional positioning in the x/y plane of the bone plate is rendered possible. The additional flexibility of the longitudinal bone plate in the z-direction, i.e. perpendicular to the x/y direction, (due to the longitudinal hole) renders possible further adjustments in the case of malpositioning of the joint of the jaw occurring after the orthognatic correction has been carried out.

The invention and further developments of the invention are explained in detail below, by means of a design model.

DETAILED DESCRIPTION OF THE PREFERRED EMBODIMENT

Figure 1:
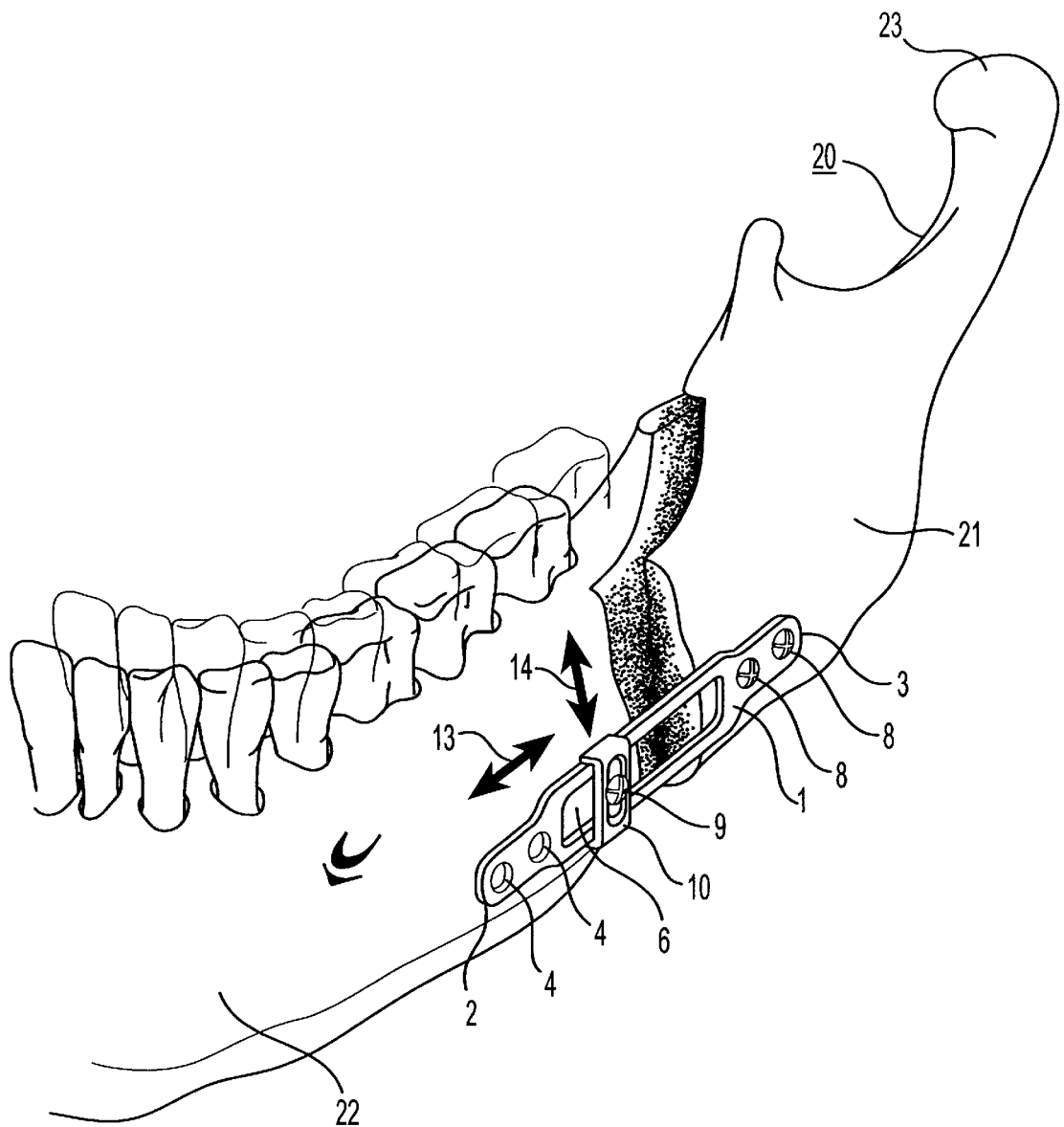
FIG. 1 shows a perspective view of the device according to the invention, mounted on a lower jaw.

The device according to the invention represented in FIG. 1 consists mainly of a longitudinal bone plate 1 and a slide 10, arranged in a movable manner on top of bone plate 1.

Figure 3:
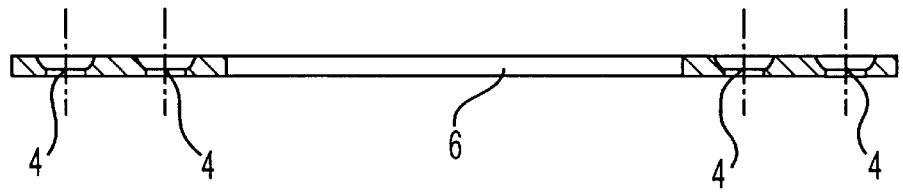
FIG. 3 shows a longitudinal section of the bone plate according to FIG. 2 along the line III—III.
Figure 2:
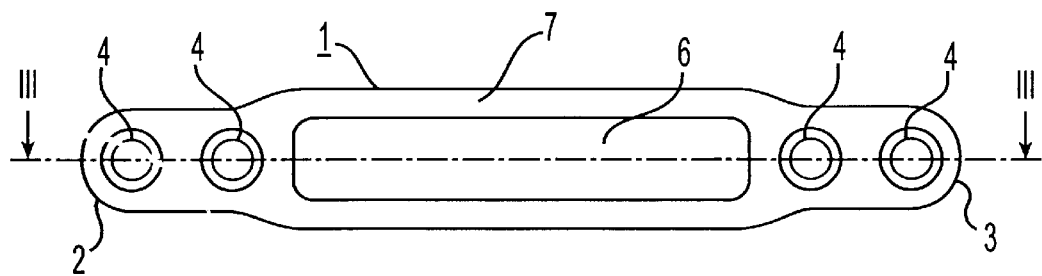
FIG. 2 shows a top plan view of the bone plate of the device according to the invention.

The longitudinal bone plate 1, shown in detail in FIG. 2 and FIG. 3, is provided at both ends 2, 3 with two through-holes 4 each; cortical screws 8 (FIG. 1) pass through these screw-holes 4 and can be screwed into the jaw bone 20. Bone plate 1 is further provided with a central longitudinal hole 6, extending in the direction of the longitudinal axis of the bone plate 1. With the total length of bone plate 1 amounting to between 30 and 50 mm (typically 44 mm), its maximum width, measured across the centre of bone plate 1, amounting to between 6–8 mm (e.g. 7 mm), and its thickness amounting to between 0.5 to 0.8 mm (e.g. 0.7 mm), for practical purposes the length of the longitudinal hole 6 is selected within the area of 18–27 mm and typically amounts to 22.8 mm; the width of the longitudinal hole 6 is selected within the area of 3–5 mm for practical purposes and typically amounts to 4 mm.

Figure 4:
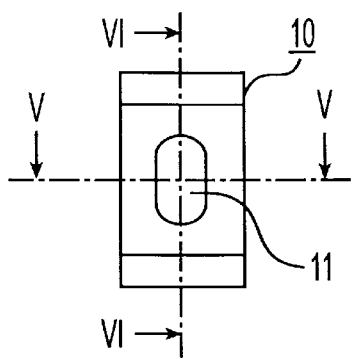
FIG. 4 shows a top plan view of the slide of the device according to the invention.
Figure 5:
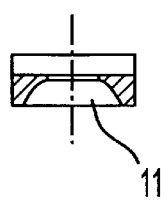
FIG. 5 shows a longitudinal section of the slide according to FIG. 4 along the line V—V.
Figure 6:
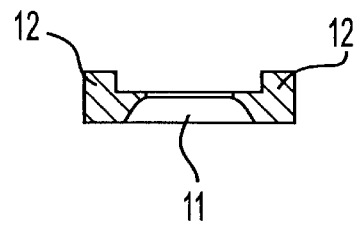
FIG. 6 shows a longitudinal section of the slide according to FIG. 4 along the line VI—VI.

Slide 10, shown in detail in FIG. 4–FIG. 6, is mainly plate-shaped as well and is provided with a longitudinal hole 11. The rails 12, positioned at each end of slide 10, are arranged and dimensioned at slide 10 in such a way that slide 10 can be placed onto the stems 7, which laterally limit the longitudinal hole 6 of bone plate 1, and can be moved in the direction of the longitudinal axis of the plate 1. When slide 10 is placed onto the plate 1, the longitudinal hole 11 of slide 10 extends cross-wise to the longitudinal axis of plate 1.

When the length of slide 10 is 9 mm, the length of the longitudinal hole 11 is selected, for practical purposes, within the area of 3–5 mm and typically amounts to 4 mm, i.e. according to the width of the longitudinal hole 6 of bone plate 1.

Figure 7:
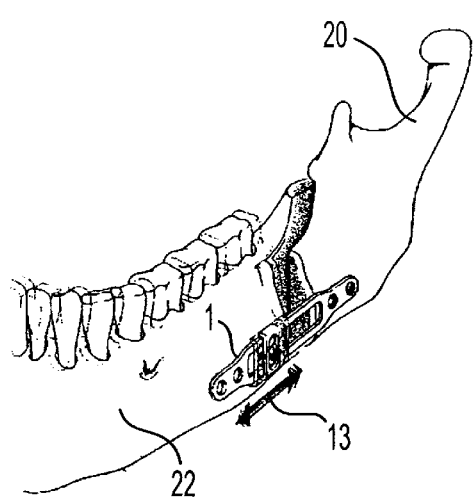
FIG. 7 shows a perspective view of the device according to the invention, mounted on a lower jaw, with the scope for intra-operative adjustment in the longitudinal direction of the bone plate.
Figure 8:
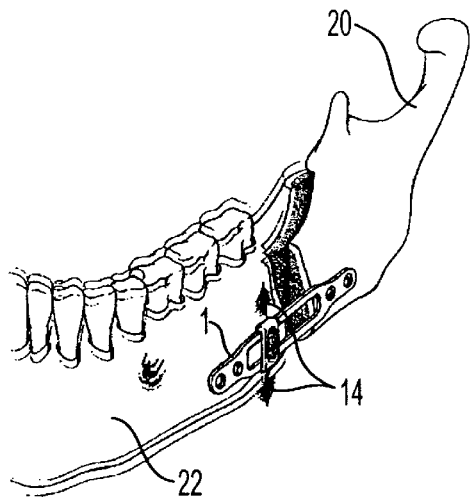
FIG. 8 shows a perspective view of the device according to the invention, mounted on a lower jaw, with the scope for intra-operative adjustment cross-wise to the bone plate.

The application of the device according to the invention for the fixation of jaw bone fragments is now described, by means of FIG. 1 as well as FIG. 7–FIG. 10, during and after a reset-osteotomy (dysgnathy) at the lower jaw. For this purpose, after a sagittal split osteotomy at the bone fragment 21 has been carried out, one of the two ends 2 of the bone plate 1 is then fixed, intra-operatively, via the bore holes 4 by means of two cortical screws 8 (monocortical screwing process in order to prevent rotation of the joint). Slide 10, positioned on the bone plate 1 in the area of the longitudinal hole 6, is temporarily fastened to the bone fragment 22 by means of screw 9—also in a monocortical manner. This position is shown in FIG. 7 and FIG. 8. Another such device according to the invention 1, 10 is fastened to the other side of the lower jaw 20 as well, this cannot be seen in FIG. 1.

Subsequently the intramaxillary immobilization is undone and the jaw is manually guided into the central joint position. If the fixation process has been carried out in the correct manner, the jaw can be guided into the occlusion projected prior to the operation. If this does not happen, the joint may either be slightly luxated, which can be noticed by an open bite, or the sagittal setting may be incorrect, which would cause a singular antagonism. If one of these cases has occurred, the screw 9 in the longitudinal hole 11 of the slide 10 is loosened and the lower jaw is then accordingly brought manually into the correct position, and screw 9 is once more fixed in its position; this process may be repeated, if necessary.

Due to the longitudinal hole 6 arranged in the longitudinal direction of the bone plate 1, and due to the longitudinal hole 11 of slide 10, arranged cross-wise to the longitudinal hole 6, a three-dimensional flexibility of the device according to the invention 1, 10 is guaranteed during the setting of the position of the jaw. This degree of flexibility exists in the x-direction indicated by arrow 13 (FIG. 7) as well as in the y-direction indicated by arrow 14 (FIG. 8).

After the exact reciprocal position (occlusion) of the upper and lower jaw has been set, screw 9 in the longitudinal hole 11 of slide 10 is drawn tight, so that slide 10 is blocked in the x-direction and in the y-direction, in relation to bone plate 1 as well as in relation to the bone fragment 22.

Figure 9:
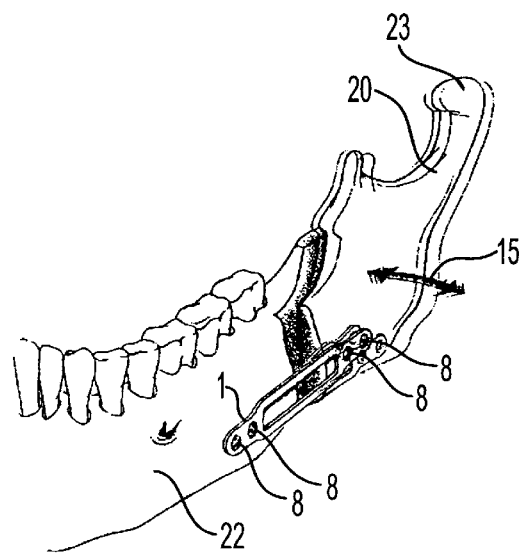
FIG. 9 shows a perspective view of the bone plate of the device according to the invention, mounted on a lower jaw, in the post-operative final position with the greatest possible scope of adjustment vertical to the plane of the bone plate.

Subsequently, as is shown in FIG. 9, two additional cortical screws 8 are guided through the still empty screw holes 4 at the other end 2 of the bone plate 1 and are fixed within the bone fragment 22, slide 10 is then removed.

The reduced thickness of bone plate 1 as compared to the thickness of the usual bone plates, as well as its relatively large width ensure its adaptability in the direction of the z-axis (arrow 15) and thus a limited correction of axis errors of the joint of the jaw 23, without loss of stiffness in the y-axis.

Figure 10:
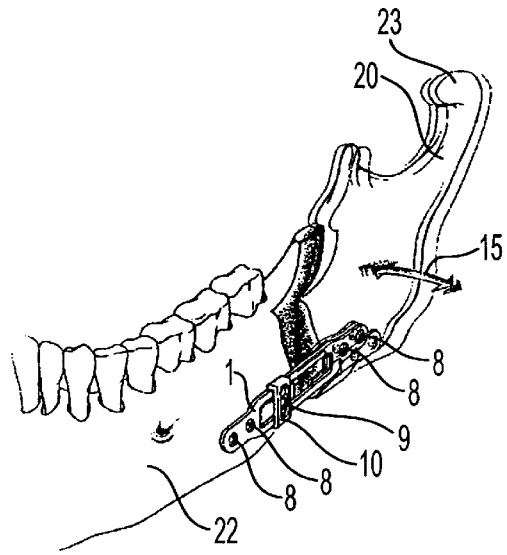
FIG. 10 shows a perspective view of the device according to the invention, mounted on a lower jaw, in the post-operative final position with the minimum scope of adjustment vertical to the plane of the bone plate.

As shown in FIG. 9, a maximum adaptability in the direction of the z-axis (arrow 15) results post-operation when the slide 10 is omitted entirely. If slide 10 is mounted, as shown in FIG. 10, there is a minimum adaptability in the direction of the z-axis (arrow 15) after the operation has been performed.

What is claimed is:

1. A device for fixation of bone fragments comprising:
   a longitudinal bone plate having a longitudinal axis, a total length, a total width, and a thickness; first and second ends each provided with at least one through-hole for receiving a screw; and a single central longitudinal hole extending in the direction of the longitudinal axis of the plate and having a width and a length amounting to 45–60% of the total length of the bone plate; and
   a slide provided and arranged on stems, said stems laterally limiting the central longitudinal hole in such a way that the slide is movable in the direction of the longitudinal axis of the plate, said slide further provided with a longitudinal hole having a length and extending cross-wise to the longitudinal axis of the plate when the slide is mounted on the bone plate,
   wherein the width of the central longitudinal hole of the bone plate and the length of the longitudinal hole of the slide are configured and dimensioned to facilitate placement of a fastener in different positions along the length of the longitudinal hole of the slide and along the width of the central longitudinal hole of the bone plate.

2. The device of claim 1, wherein the width of the central longitudinal hole amounts to 50–65% of the total width of the bone plate.

3. The device of claim 1, wherein the length of the longitudinal hole of the slide essentially corresponds to the width of the central longitudinal hole.

4. The device of claim 1 wherein the thickness of the bone plate amounts to 8–12% of the total width of the bone plate and wherein at least two through-holes are provided on each end of the bone plate.

5. The device of claim 1 in combination with a fastener having a diameter that is smaller than the length of the longitudinal hole of the slide.

* * * * *